United States Patent [19]

Vanlerberghe et al.

[11] 4,456,586

[45] Jun. 26, 1984

[54] NON-IONIC SURFACE-ACTIVE AGENTS DERIVED FROM GLUCOSE, PROCESS FOR THEIR PREPARATION AND COMPOSITIONS CONTAINING THEM

[75] Inventors: Guy Vanlerberghe, Claye-Souilly; Henri Sebag, Paris; Rene Pierre, Aulnay-sous-Bois, all of France

[73] Assignee: L'Oreal, Paris, France

[21] Appl. No.: 314,400

[22] Filed: Oct. 23, 1981

[30] Foreign Application Priority Data

Oct. 24, 1980 [FR] France ................. 80 22885

[51] Int. Cl.³ .................. A61K 7/06; C07G 3/00
[52] U.S. Cl. .................. 424/70; 260/239.55 R; 424/DIG. 1; 424/DIG. 2; 424/DIG. 4; 424/47; 424/59; 424/65; 424/68; 424/69; 424/78; 424/180; 424/358; 424/365; 536/120; 549/435; 549/472
[58] Field of Search .......... 536/120, 18.6, 18.3, 536/4; 424/47, 365, 180; 549/435, 472; 260/239.55 R

[56] References Cited

U.S. PATENT DOCUMENTS 4,056,322 11/1977 Gordon et al. .................. 536/4
4,217,344 8/1980 Vanlerberghe et al. .......... 424/60

FOREIGN PATENT DOCUMENTS 1063908 6/1976 Canada .
2315991 1/1977 France .
1539625 1/1979 United Kingdom .

OTHER PUBLICATIONS

Vischer et al., *Helv. Chim. Acta* 27, 1,332–45 (1944).

*Primary Examiner*—Dale R. Ore
*Attorney, Agent, or Firm*—Fleit, Jacobson, Cohn & Price

[57] ABSTRACT

Non-ionic surface-active agents of the formula are disclosed:

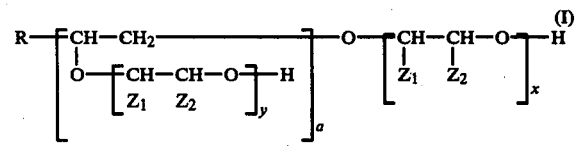

in which $a=0$ or 1, R denotes a $C_8$-$C_{30}$ aliphatic or alicyclic radical, $x+y$ totals a number from 1 to 10 and, in each unit, one of $Z_1$ and $Z_2$ denotes hydrogen and the other denotes the radical

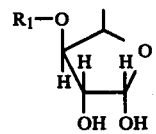

in which $R_1$ denotes methyl or ethyl.

These products can be prepared simply and are suitable for use in cosmetic or pharmaceutical compositions and in particular in cosmetic compositions for treating the hair or skin.

35 Claims, No Drawings

NON-IONIC SURFACE-ACTIVE AGENTS DERIVED FROM GLUCOSE, PROCESS FOR THEIR PREPARATION AND COMPOSITIONS CONTAINING THEM

DESCRIPTION

The present invention relates to non-ionic surface-active agents derived from glucose, which are soluble or dispersible in water, a process for their preparation and their use in cosmetic and pharmaceutical compositions.

The preparation of surface-active agents derived from sugars, in particular sucrose esters or polyglycoside ethers, has already been described.

However, these compounds are very difficult to prepare as a result of the absence of contact for reaction between, on the one hand, the glucose or another water-soluble sugar, and, on the other hand, the hydrophobic fatty acids or alcohols. To overcome these difficulties, it has been proposed to use various solvents, but, in numerous cases, these solvents are toxic, unstable or difficult to remove.

Moreover, in view of the fact that sugars contain several hydroxyl groups, the esterification, etherification or acetalisation reactions are random reactions and consequently difficult to control in a suitable way. Another significant disadvantage of these products is the chemical instability, in basic or acid solution, of the group joining the fatty chain to the hydrophilic part.

We have now discovered according to this invention, a new class of surface-active agents derived from glucose, which do not exhibit such disadvantages to any significant degree.

The products of the invention can be represented by the general formula (I)

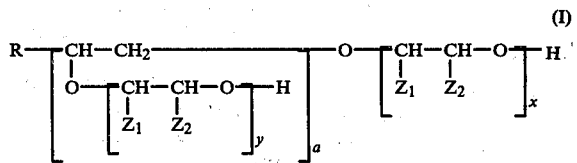

in which: a denotes zero or 1, R denotes a saturated or unsaturated, linear or branched aliphatic radical or an alicyclic radical containing 8 to 30 carbon atoms, and preferably a linear or branched alkyl or alkenyl radical having from 8 to 18 carbon atoms, an alkylphenyl radical, the alkyl part of which contains 8 to 12 carbon atoms, or a radical derived from a sterol having up to 30 carbon atoms, (x+y) denotes an integer or decimal number from 1 to 10, representing an average statistical value, and $Z_1$ and $Z_2$ denote, in each unit, in one case a hydrogen atom and in the other case the radical:

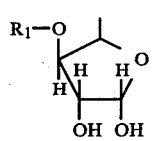

in which $R_1$ denotes methyl or ethyl.

If a denotes 1, R generally denotes an aliphatic radical having from 8 to 18 carbon atoms, and preferably a linear alkyl radical having from 8 to 18 carbon atoms.

This radical (V) will hereafter be designated for simplicity as $R_1$—A, in which A denotes the group:

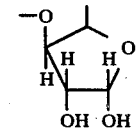

The products of the formula (I) can be obtained by the telomerisation, in a first step, of an epoxide of the formula (II)

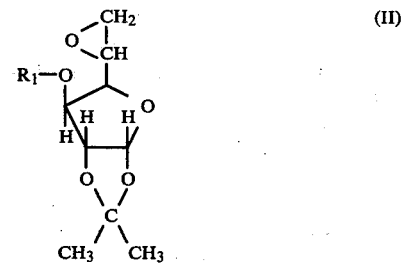

with, as the telogen containing active hydrogen, one or more alcohols, alkane-1,2-diols or alkylphenols of the formula (III)

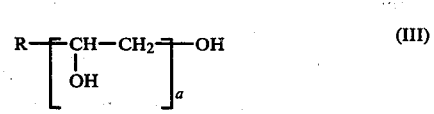

R and a being as defined above.

The intermediates obtained in this first step can be represented by the general formula (IV) below:

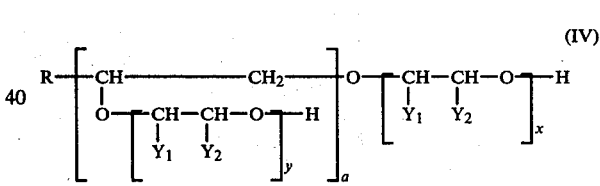

in which R, a, x and y have the same meaning as for (I) and, in each unit, one of $Y_1$ and $Y_2$ denotes a hydrogen atom and the other denotes the radical:

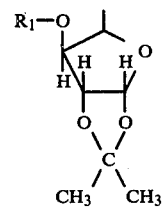

In a second step the intermediates IV are hydrolysed in acid solution to give rise to the products of this invention.

The following alcohols may be mentioned as preferred compounds of formula III: octanol, decanol, dodecanol, tetradecanol, hexadecanol, octadecanol, eicosanol, 2-methyldodecanol, 2-methyltridecanol, 2-methyltetradecanol, 2-methylpentadecanol, 2-ethylhexanol, 2-butyloctanol, 2-hexyldecanol, 2-octyldodecanol, oleyl alcohol, lanolin alcohols, cholesterol or beta-sitosterol, dodecylbenzyl alcohol, alkanediols such as octane-1,2-diol, decane-1,2-diol, dodecane-1,2-diol, tetradecane-1,2-diol, hexadecane-1,2-diol, octadecane-1,2-diol and eicosane-1,2-diol, and phenols such as octylphenol and nonykphdnol.

The 5,6-epoxy-3-alkoxy-1,2-isopropylideneglucoses of the formula (II) can be obtained in accordance with known processes (see e.g. E. VISCHER and T. REICHSTEIN, Helv. Chim. Acta 27, 1,332-45 (1944)).

The telomerisation reactions are suitably carried out in the presence of, say, 0.2 to 3% by weight of a Lewis acid catalyst such as $BF_3$ or $SnCl_4$, or in the presence of 0.2 to 15% of a basic catalyst such as sodium, potassium, sodium methylate or ethylate or potassium methylate or ethylate, the percentages being expressed relative to the total weight of the reactants.

In acid catalysis, the polyaddition reactions are suitably carried out at a temperature of 20° C. to 120° C. and preferably 40° to 80° C. In alkaline catalysis, the temperature is suitably 120° to 160° C.

These telomerisation reactions can be carried out in the presence of absence of solvents. The latter, which can be introduced, in particular, for reasons of convenience when the amounts of the reactants used are small, are generally inert solvents which are easy to remove, such as hexane or heptane in acid catalysis and methyl ethyl ketone or methyl isobutyl ketone in basic catalysis.

During the telomerisation reactions constituting the first step of the process, a mixture of compounds is formed, which all correspond to the formula (IV), but in which the number of molecules of epoxide of the formula (II) which are fixed can be greater or less than the average statistical value corresponding to the number of molecules of epoxide used per molecule of compound of the formula (III).

Moreover, two isomers are generally formed depending on the direction of opening of the oxirane ring, which can open in two different ways.

The different isomers are represented by the general formula IV, in which, for each unit, one of the groups $Y_1$ or $Y_2$ denotes the radical:

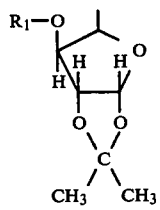

and the other denotes a hydrogen atom.

The second step of the preparation is a hydrolysis reaction of the isopropylidene groups of the compounds of the formula IV, which can be carried out in the presence of an aqueous solution of, say, sulphuric, hydrochloric or acetic acid and, if appropriate, in the presence of a water-soluble solvent such as methanol, ethanol, isopropanol or t-butanol, generally at a temperature from 20° to 100° C., with the formation of the products of this invention.

In view of the process of preparation and the epoxide reactant II used, in which all the other sites are blocked, the telomers of the invention are all products containing a single hydrocarbon chain and one or two hydrophilic chains, depending on whether the telogen III contains one or two hydroxyl groups.

The chemical linkages between the hydrocarbon chain and the hydrophilic chain or hydrophilic chains, on the one hand, and the linkages between the various units of the latter, on the other hand, are all ether bonds which are perfectly stable in acid or basic solution. As a result, the compounds of formula I are stable in acid or basic solution. The hydrophilic chains are linear polyether chains containing the pendent groups:

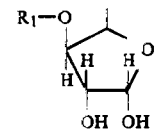

but no branching.

The products of formula (I) are in the form of a liquid, paste or powder.

Depending on the nature of the starting compound (III) and on the value of $x+y$, these products are either dispersible or soluble in water.

They can be used in various cosmetic compositions, usually in the presence of a suitable vehicle, and in particular in cosmetic compositions for treating the hair or skin, or in pharmaceutical compositions.

The vehicle is advantageously water, an aqueous-alcoholic solution, the alcohol preferably having from 1 to 6 carbon atoms, an animal, vegetable, mineral or synthetic oil, an oil-in-water or water-in-oil emulsion or an oily-aqueous suspension.

In these compositions, the products of the invention most frequently act as cleansing agents, dispersing agents, emulsifiers, solubilising agents or emollients. They can also act as carriers of the active product or can constitute the base of a cosmetic or phrmaceutical composition.

The compositions suitably contain from 0.05 to 100% by weight, and preferably from 0.2 to 20% by weight, of at least one product of the formula (I), relative to the total weight of the composition.

The cosmetic and pharmaceutical compositions are generally in the form of an aqueous solution, aqueous-alcoholic solution, emulsion, powder, wax, microemulsion, gel, oil, oily-alcoholic composition, aerosol or aqueous or oily-aqueous dispersion of lipids.

Amongst the cosmetic compositions, compositions for the treatment and care of the skin and hair should be mentioned more particularly.

Amongst typical compositions for treating the hair, which can contain the products of this invention, there may be mentioned shampoos, rinsing solutions or lotions, leave-on lotions, wavesetting lotions and dyeing compositions; amongst compositions for the treatment and care of the skin, there may be mentioned emulsions or milks and creams for treating the body and/or face, sun protection products, and aqueous or oily-aqueous dispersions of lipids capable of carrying active substances.

These compositions contain, in a suitable vehicle or base, a product of formula (I), if appropriate associated with one or more compounds such as non-ionic, anionic, cationic, amphoteric or zwitterionic surface-active agents, animal, mineral, vegetable or synthetic oils or waxes, anionic, cationic, non-ionic or amphoteric resins normally used in cosmetics, thickeners, opacifiers, preservatives, perfumes, dyestuffs, inorganic salts, natural or synthetic lipids, alcoholic solvents having from 1 to 6 carbon atoms, pH modifiers, natural substances, sun filters, and active substances which can have an action in the treatment, care or protection of the skin or hair.

The products according to the invention can also form, in an aqueous medium, the walls of small lipid spheres which can be used for carrying the active products, in particular cosmetic and pharmaceutical active products.

Apart from the substance to be carried, they can in this case be associated with compounds capable of modifying the permeability of the lipid capsule which they form around the active substance. Amongst these compounds modifying the permeability of the lipid capsule, sterols such as cholesterol or sitosterol, and ionic lipid compounds such as sodium dicetyl-phosphate or dimethyldistearylammonium chloride or bromide, may be mentioned more particularly.

Amongst the active products which can be carried in the lipid membranes, there may be mentioned humectants, agents for artificial bronzing of the skin, sun filters, antiperspirants, deodorants, astringents, scented waters, freshening products, tonics, cicatrising agents, keratolytic agents, depilatories, animal or plant tissue extracts, water-soluble dyestuffs, anti-dandruff agents, anti-seborrhoea agents and reducing agents.

Amongst the pharmaceutical active products, there may be mentioned: vitamins, hormones, enzymes, vaccines, anti-inflammatory products, antibiotics, bactericides and corticoids.

Processes for obtaining the small lipid spheres are described in, for example, French Patent Application No. 2,315,991, British Patent Specification No. 1,539,625, Canadian Patent No. 1,063,908, Belgian Patent No. 843,300 and U.S. Pat. No. 4,217,344, the disclosure of all of which is hereby incorporated by reference.

This invention also provides a process for the cosmetic treatment of the hair or skin, characterised in that a suitable amount of a composition described above is applied to the hair or skin.

The following Examples further illustrate the present invention.

1,2-Isopropylidene-5,6-anhydro-d-glucose 3-methyl ether (compound (IIa)) and 1,2-isopropylidene-5,6-anhydro-d-glucose 3-ethyl ether (compound (IIb)) are prepared in accordance with the method described by E. VISCHER and T. REICHSTEIN in Helv. Chim. Acta 27, 1,332–45 (1944).

The compound (IIa) is in the form of a colourless oil having a boiling point of 80°–85° C. under a reduced pressure of 6.65 pascals, and an epoxide number of 4.70 milliequivalents/g.

The compound (IIb) is in the form of a colourless oil having a boiling point of 87° C. under a reduced pressure of 1.33 pascals.

These two compounds are characterised by vapour phase chromatography, by their infra-red spectrum and by their nuclear magnetic resonance (NMR) spectrum.

EXAMPLE 1

Preparation of a mixture of compounds of the formula I in which: R denotes the radical $C_{12}H_{25}$, a denotes zero, either $Z_1$ or $Z_2$ denotes the group $CH_3$—A and x denotes an average statistical value of 4.

0.04 ml of $BF_3$ etherate is added, at 50° C., to 1 g (0.0055 mol) of dodecan-1-ol dissolved in 4 ml of heptane, and 4.80 g (0.022 mol) of compound (IIa) diluted with 2 ml of heptane are then added in the course of 30 minutes.

The reaction medium is subsequently kept at 50° C. for 4 hours and then washed with 2 times 10 ml of a saturated solution of sodium bicarbonate and then with 5 ml of water.

The heptane is removed by heating under reduced pressure.

The residue is taken up in 12 ml of isopropanol containing 6 ml of N hydrochloric acid. The solution is heated under reflux for 5 hours 30 minutes. 8 ml of water are added gradually.

The mixture is concentrated under reduced pressure and the remaining acid is neutralised with 2.6 ml of N NaOH solution to pH 7.

The solution is then demineralised by stirring with an ion exchange resin, and adjusted to an active ingredient content of 20%.

The cloud point of a 0.5% strength solution in water containing 10% of NaCl is above 100° C.; in a solution containing 25% of NaCl, the cloud point is 66° C.

EXAMPLE 2

Preparation of a mixture of compounds of the formula I in which: R denotes the radical $C_{16}H_{33}$, a denotes zero, either $Z_1$ or $Z_2$ denotes the group $CH_3$—A and x denotes an average statistical value of 1.5.

0.06 ml of $BF_3$ etherate is added to 4.84 g (0.02 mol) of hexadecan-1-ol dissolved in 10 ml of heptane, and 6.48 g (0.03 mol) of compound (IIa) dissolved in 30 ml of heptane are then added at 60° C., in the course of 30 minutes. The reaction medium is heated for 4 hours at 65° C.

The solvent is evaporated off under reduced pressure and the residue is taken up in 20 ml of isopropanol and 5 ml of N hydrochloric acid over a period of 4 hours, at the reflux temperature. 10 ml of water are added gradually during the heating.

The mixture is neutralised with N NaOH solution and evaporated to dryness. The residue is taken up in 50 ml of hot isopropanol. After the sodium chloride has been filtered off, the filtrate is again evaporated to dryness.

This yields a yellow solid which is dispersible in hot water.

Melting point: 65° C.

EXAMPLE 3

Preparation of a mixture of compounds of the formula I in which: R denotes the radical $C_{16}H_{33}$, a denotes zero, either $Z_1$ or $Z_2$ denotes the group $CH_3$—A and x denotes an average statistical value of 4.

0.06 ml of $BF_3$ etherate is added to 2.42 g (0.01 mol) of hexadecan-1-ol dissolved in 15 g of heptane, and 8.64 g (0.04 mol) of epoxide (IIa) are then added at 50° C., in the course of 30 minutes.

The heating is maintained for 3 hours and the solvent is then removed under reduced pressure.

The residue is taken up under reflux in 20 ml of isopropanol and 20 ml of N/2 HCl over a period of 8 hours.

During the heating, 100 ml of water are added gradually. The mixture is neutralised by adding 10 ml of N NaOH solution and demineralised by stirring in the presence of a mixed ion exchange resin.

After evaporation to dryness, a hygroscopic white solid is obtained which is soluble in water.

EXAMPLE 4

Preparation of a mixture of compounds of the formula I in which: R denotes the hydrocarbon radical of cholesterol, a denotes zero, either $Z_1$ and $Z_2$ denotes the group $CH_3$—A— and x denotes an average statistical value of 2.

3.86 g (0.01 mol) of recrystallised cholesterol are dissolved in 15 ml of heptane at 60° C.

After the addition of 0.035 ml of $BF_3$ etherate, 4.32 g (0.02 mol) of epoxide (IIa) diluted with 20 ml of heptane are added.

After heating for 3 hours at 60° C., the reaction is complete; the solvent is removed under reduced pressure.

The residue is hydrolysed by heating in 5 ml of isopropanol and 5 ml of normal hydrochloric acid at 80° C.

After neutralisation, separation of the sodium chloride and evaporation to dryness, a white powder is obtained which gives a gel in water.

Melting point: 98° C.

Cloud point in water containing 10% of NaCl: 62° C.

EXAMPLE 5

Preparation of a mixture of compounds of the formula I in which: R denotes the hydrocarbon radical of cholesterol, a denotes zero, either $Z_1$ or $Z_2$ denotes the group $CH_3$—A and x denotes an average statistical value of 4.

3.86 g (0.01 mol) of cholesterol are dissolved in 20 g of heptane at 60° C. After the addition of 0.07 ml of $BF_3$ etherate, 8.64 g (0.04 mol) of compound (IIa) are added in the course of 30 minutes and the mixture is heated for 3 hours.

After evaporation to dryness, a white powder is obtained.

This powder is solubilised in 100 ml of acetic acid in the presence of 20 ml of N sulphuric acid.

The mixture is heated at 80° C. for 30 minutes.

The sulphuric acid is neutralised with 47.5 ml of 0.42 N barium hydroxide solution.

The barium salt is separated off by centrifugation.

The acetic acid is then distilled after the addition of 600 ml of toluene.

After drying, a white powder is obtained which is soluble in water.

Cloud point in water containing 10% NaCl: 82° C.

EXAMPLE 6

Preparation of a mixture of compounds of the formula I in which: R denotes the radical $C_{10}H_{21}$, a denotes 1, either $Z_1$ or $Z_2$ denotes the group $CH_3$—A and (x+y) denotes an average statistical value of 2.

0.14 g of sodium methylate dissolved in methanol (0.79 milliequivalent) is added to 2 g (0.01 mol) of molten dodecane-1,2-diol, and 6.48 g (0.03 mol) of compound (IIa) diluted with 28 g of heptane are then added under a nitrogen atmosphere, at 150° C. The solvent is distilled under a partial vacuum throughout the addition.

The addition lasts 30 minutes and the heating is maintained for a further 30 minutes at 150° C.

The reaction mixture is heated under reflux in a mixture of 5 ml of isopropanol and 2.5 ml of N hydrochloric acid.

During the 4 hours of heating, 30 ml of water are added gradually. The mixture is neutralised with 2.5 ml of N NaOH solution and the resulting solution is decolorised by stirring with 1 g of decolorising charcoal. After filtration and demineralisation, the filtrate is evaporated to dryness and this yields a light brown solid product which is soluble in water.

The cloud point of a 0.5% strength aqueous solution is above 100° C.

EXAMPLE 7

Preparation of a mixture of compounds of the formula I in which: R denotes the radical $C_{12}H_{25}$, a denotes zero, either $Z_1$ or $Z_2$ denotes the group $C_2H_5$—A and x denotes an average statistical value of 4.

0.06 ml of $BF_3$ etherate is added to 1.4 g (0.0075 mol) of dodecan-1-ol dissolved in 6 ml of heptane, and 6.9 g (0.03 mol) of compound (IIb) diluted with 40 ml of heptane are then added at 60° C. The mixture is heated for a further 5 hours at 60° C. The reaction is then complete.

The solvent is removed under reduced pressure.

The residue is taken up in 20 ml of isopropanol and 5 ml of N HCl and the solution is heated under reflux for 4 hours, 10 ml of water being added gradually.

The mixture is neutralised with N NaOH solution, the sodium chloride is separated off and the solution is evaporated to dryness.

This yields a solid which is soluble in water.

The cloud point of a 0.5% strength solution is 58° C.

EXAMPLE 8

Preparation of a mixture of compounds of the formula I in which: R denotes the nonylphenyl radical, a denotes zero, either $Z_1$ or $Z_2$ denotes the group $CH_3$—A and x denotes an average statistical value of 6.

0.35 ml of $BF_3$ etherate is added, at 60° C., to 6.6 g (0.03 mol) of nonylphenol, and 38.8 g (0.18 mol) of compound (IIa) diluted in 185 g of heptane are then added in the course of 1 hour.

After the solvent has been evaporated off, the solid residue is taken up in 210 ml of isopropanol in the presence of 60 ml of N HCl, and the mixture is heated at 70° C. for 8 hours.

It is neutralised by the addition of 60 ml of N NaOH solution.

The isopropanol and the water are then distilled and the residue is again taken up in isopropanol.

The sodium chloride is filtered off and the filtrate is then evaporated to dryness. This yields a yellow powder which is soluble in water.

The cloud point of a 0.5% strength aqueous solution is above 100° C.

EXAMPLE 9

Preparation of a mixture of compounds of the formula (I) in which R denotes the hydrocarbon radical of oleyl alcohol, a denotes zero, either $Z_1$ or $Z_2$ denotes the group $C_2H_5$—A and x denotes an average statistical value of 9.

0.1 ml of tin tetrachloride is added to 3.6 g (0.013 mol) of oleyl alcohol dissolved in 60 ml of heptane, and 27.6 g (0.12 mol) of epoxide (IIb) diluted with 160 ml of heptane are then added dropwise, at 60° C., in the course of 1 hour.

The heating and stirring are maintained for 3 hours after the addition.

The complete disappearance of the compound (IIb) is checked by thin layer chromatography.

The solvent is removed by evaporation under reduced pressure. The residue is taken up in 80 ml of isopropanol and 20 ml of 1N hydrochloric acid and the mixture is then heated at 80° C. for 6 hours, whilst at the same time gradually introducing 80 ml of water.

The hydrochloric acid is exactly neutralised with 1N NaOH solution.

After evaporation to dryness, the residue is again taken up in 100 ml of isopropanol. The sodium chloride is removed by filtration.

The mixture is then evaporated to dryness.

After grinding, the product obtained is in the form of a sandy yellow powder which is soluble in water.

The cloud point of a solution containing 0.5% of active ingredient is 63° C.

APPLICATION EXAMPLES

EXAMPLE A1

| Body milk | |
|---|---|
| Mixture of compounds of Example 7 | 4 g |
| Cholesterol | 3.6 g |
| Dicetyl phosphate | 0.4 g |
| Sodium salt of pyrrolidonecarboxylic acid | 2 g |
| Water q.s.p. | 100 g |

EXAMPLE A2

| Hand cream | |
|---|---|
| Mixture of compounds of Example 2 | 4 g |
| Beta-sitosterol | 3.6 g |
| Dicetyl phosphate | 0.4 g |
| 0.3 M glycerol q.s.p. | 100 g |

EXAMPLE A3

| Day cream | |
|---|---|
| Mixture of compounds of Example 4 | 4 g |
| Cholesterol | 4 g |
| Water q.s.p. | 100 g |

EXAMPLE A4

| Body milk | |
|---|---|
| Mixture of compounds of Example 7 | 10 g |
| Liquid petrolatum | 40 g |
| Water q.s.p. | 100 g |

The mixture of compounds obtained in accordance with Example 7 is introduced into the petrolatum 50 g of water are then added and the mixture is agitated by ultrasound. This gives an oil-in-water emulsion having the appearance of a milk.

EXAMPLE A5

| Hair lotion | |
|---|---|
| Mixture of compounds of Example 8 | 0.2 g |
| Vinyl acetate/crotonic acid/polyethylene glycol terpolymer (sold under the name "ARISTOFLEX A" by HOECHST) | 2 g |
| Ethanol | 10% by volume |
| 2-Amino-2-methylpropanol q.s.p. | pH 8.8 |
| Water q.s.p. | 100 ml |

EXAMPLE A6

| Hair lotion | |
|---|---|
| Mixture of compounds of Example 5 | 0.5 g |
| Quaternary polyvinylpyrrolidone copolymer having a molecular weight of about 1,000,000 (sold under the name of "GAFQUAT 734" by General Aniline) | 1 g of active ingredient |
| Water q.s.p. | 100 ml |

EXAMPLE A7

| Hair lotion | |
|---|---|
| Mixture of compounds of Example 8 | 0.5 g |
| Quaternary vinylpyrrolidone copolymer having a molecular weight of about 1,000,000 (sold under the name of "GAFQUAT 734" by General Aniline) | 0.8 g of active ingredient |
| Water q.s.p. | 100 ml |

EXAMPLE A8

| Hair lotion | |
|---|---|
| Mixture of compounds of Example 8 | 0.3 g |
| Vinylpyrrolidone/vinyl acetate copolymer (60/40) | 3.0 g |
| Ethanol | 20% by volume |
| Water q.s.p. | 100 ml |

We claim:

1. A non-ionic surface-active product of the formula:

$$R-\left[CH-CH_2-\left[O-\left[CH-CH-O\right]_y-H\right]_a-O-\left[CH-CH-O\right]_x-H \atop Z_1 \quad Z_2\right] \quad (1)$$

in which: a denotes zero or 1, R denotes a saturated or unsaturated, linear or branched aliphatic radical or an alicyclic radical containing 8 to 30 carbon atoms, x and y each denote zero or a positive number such that (x+y) denotes an integral or non-integral number from 1 to 10, and in each unit $-CHZ_1-CHZ_2-O-$ one of $Z_1$ and $Z_2$ denotes a hydrogen atom and the other the radical:

$$-R_1-O-\underset{OH \quad OH-}{\underset{H}{\overset{H}{\bigvee}}}\overset{H}{\underset{}{\bigvee}}O$$

in which $R_1$ denotes methyl or ethyl.

2. A product according to claim 1, in which a denotes zero and R denotes a linear or branched alkyl or alkenyl radical having from 8 to 18 carbon atoms, an alkylphenyl radical, the alkyl part of which contains 8 to 12 carbon atoms, or a radical derived from a sterol having up to 30 carbon atoms.

3. A product according to claim 1, in which a denotes 1, and R denotes a linear alkyl radical having from 8 to 18 carbon atoms.

4. A product according to claim 1 or 2, in which a denotes zero and R denotes an octyl, decyl, dodecyl, tetradecyl, hexadecyl, octadecyl, eicosyl, 2-methyldodecyl, 2-methyltridecyl, 2-methyltetradecyl, 2-methylpentadecyl, 2-ethylhexyl, 2-butyloctyl, 2-hexyldecyl, 2-octyldodecyl, oleyl, cholesterol or beta-sitosterol radical, a radical of a lanolin alcohol or a dodecylbenzyl, octylphenyl or nonylphenyl radical.

5. A product according to claim 1 or 3, in which a denotes 1 and R denotes an octyl, decyl, dodecyl, tetradecyl, hexadecyl, octadecyl or eicosyl radical.

6. A product of the formula

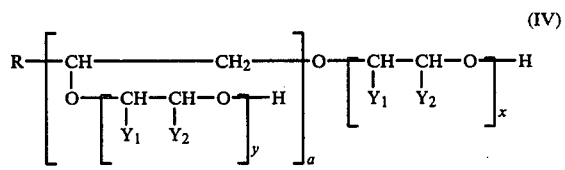

in which R, a, x and y are as defined in claim 1 and one of $Y_1$ and $Y_2$ denotes, in each unit, a hydrogen atom and the other the radical of formula:

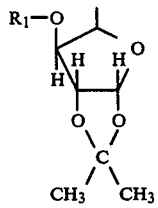

in which $R_1$ denotes methyl or ethyl.

7. Process for the preparation of a product as defined in claim 1 which comprises hydrolysing in acid solution a product as defined in claim 6.

8. Process according to claim 7, in which the hydrolysis is carried out in the presence of an aqueous sulphuric acid, hydrochloric acid or acetic acid, at a temperature from 20° to 100° C., optionally in the presence of an alcohol having from 1 to 4 carbon atoms.

9. Process according to claim 7 in which the product as defined in claim 6 is prepared by the telomerisation of an epoxide of the formula:

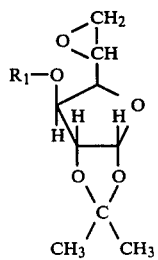

in which $R_1$ denotes methyl or ethyl, with a compound of the formula:

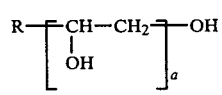

in which R and a are as defined in claim 1.

10. Process according to claim 9 in which the telomerisation reaction is carried out in the presence of a Lewis acid catalyst at a temperature from 20° to 120°.

11. Process according to claim 10 in which the telomerisation reaction is carried out in the presence of $BF_3$ or $SnCl_4$ at a temperature from 40° to 80° C.

12. Process according to claim 9 in which the telomerisation reaction is carried out in the presence of a basic catalyst at a temperature from 120° to 160° C.

13. Process according to claim 12 in which the basic catalyst is sodium, potassium, sodium methylate or ethylate or potassium methylate or ethylate.

14. Process according to claim 9 in which the telomerisation is carried out in the presence of an inert solvent.

15. Process according to claim 14, in which the telomerisation is carried out in the presence of a Lewis acid catalyst and the solvent is hexane or heptane, or in the presence of a basic catalyst and the solvent is methyl ethyl ketone or methyl isobutyl ketone.

16. A non-ionic surface-active product of the formula:

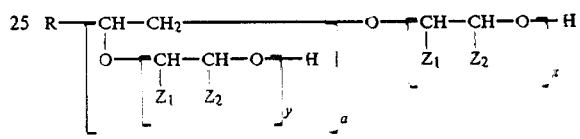

in which: a denotes zero, R denotes a saturated or unsaturated, linear or branched aliphatic radical or an alicyclic radical containing 8 to 30 carbon atoms, x denotes an integral or non-integral number from 1 to 10, and in each unit —$CHZ_1$—$CHZ_2$—O—, one of $Z_1$ and $Z_2$ denotes a hydrogen atom and the other the radical:

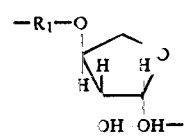

in which $R_1$ denotes methyl or ethyl.

17. A product according to claim 16 in which R denotes a linear or branched alkyl or alkenyl radical having from 8 to 18 carbon atoms.

18. A product according to claim 16, in which R denotes an alkylphenyl radical, the alkyl part of which contains 8 to 12 carbon atoms.

19. A product according to claim 16, in which R denotes a radical derived from a sterol, having up to 30 carbon atoms.

20. A product according to claim 16, in which R denotes a radical derived from cholesterol.

21. A product according to claim 16, in which R denotes a linear or branched alkyl or alkenyl radical having from 8 to 18 carbon atoms, an alkylphenyl radical, the alkyl part of which contains 8 to 12 carbon atoms, or a radical derived from a sterol having up to 30 carbon atoms.

22. A product according to claim 16, in which R denotes an octyl, decyl, dodecyl, tetradecyl, hexadecyl, octadecyl, eicosyl, 2-methyldodecyl, 2-methyltridecyl, 2-methyltetradecyl, 2-methylpentadecyl, 2-ethylhexyl, 2-butyloctyl, 2-hexyldecyl, 2-octyldodecyl, oleyl, cholesterol or beta-sitosterol radical, a radical of a lanolin alcohol or a dodecylbenzyl, octylphenyl or nonylphenyl radical.

23. A product according to claim 16, in which R denotes the radical $C_{12}H_{25}$; x denotes an average statistical value of 4 and in each unit $-CHZ_1-CHZ_2-O-$, one of $Z_1$ and $Z_2$ denotes a hydrogen atom and the other the radical:

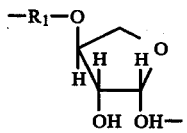

in which $R_1$ denotes methyl or ethyl.

24. A product according to claim 23, in which $R_1$ denotes methyl.

25. A product according to claim 16, wherein R denotes the radical $C_{16}H_{33}$, $R_1$ denotes the group $CH_3-$, and x denotes an average statistical value of 1.5.

26. A product according to claim 16, wherein R denotes the radical $C_{16}H_{33}$, $R_1$ denotes the group $CH_3-$, and x denotes an average statistical value of 4.

27. A product according to claim 16, wherein R denotes the hydrocarbon radical of cholesterol, $R_1$ denotes the group $CH_3-$, and x denotes an average statistical value of 2.

28. A product according to claim 16, wherein R denotes the hydrocarbon radical of cholesterol, $R_1$ denotes the group $CH_3-$, and x denotes an average statistical value of 4.

29. A product according to claim 16, wherein R denotes the radical $C_{12}H_{25}$, $R_1$ denotes the group $C_2H_5-$, an x denotes an average statistical value of 4.

30. A product according to claim 16, wherein R denotes the nonylphenyl radical, $R_1$ denotes the group $CH_3-$, and x denotes an average statistical value of 6.

31. A composition for treating hair or skin comprising at least 0.2 to 20% by weight of at least one product as defined in claim 1 and a cosmetic carrier.

32. A composition according to claim 31, which is in the form of an aqueous solution, an aqueous-alcoholic solution, an emulsion, a powder, a wax, a microemulsion, a gel, or an oil.

33. A composition according to claim 31, which also contains at least one non-ionic, anionic, cationic or amphoteric surface-active agent, animal, mineral, vegetable or synthetic oil or wax, anionic, cationic, non-ionic or amphoteric cosmetic resin, thickener, opacifier, preservative, perfume, inorganic salt, natural or synthetic lipid, solvent, or pH modifier.

34. A composition according to claim 31 for the care of the hair which is in the form of a, a hair lotion.

35. Process for the cosmetic treatment of the hair or skin, which comprises applying thereto a cosmetic composition as defined in claim 31.

* * * * *